US006878846B2

(12) United States Patent
Cowan et al.

(10) Patent No.: US 6,878,846 B2
(45) Date of Patent: Apr. 12, 2005

(54) SOLVENT SYSTEMS

(75) Inventors: Justin Mark Cowan, Kidderminster (GB); Christopher John Harris, Worcester (GB); Michael John Harrison, Stafford (GB)

(73) Assignee: Rhodia Consumer Specialties Ltd., Oldbury (GB)

( * ) Notice: Subject to any disclaimer, the term of this patent is extended or adjusted under 35 U.S.C. 154(b) by 0 days.

(21) Appl. No.: 10/177,130

(22) Filed: Jun. 21, 2002

(65) Prior Publication Data

US 2003/0013918 A1 Jan. 16, 2003

(30) Foreign Application Priority Data

Jun. 28, 2001 (GB) ............................................ 0115824

(51) Int. Cl.$^7$ ................................................ C07C 9/38
(52) U.S. Cl. ........................................ 562/13; 546/22
(58) Field of Search ............................... 546/22; 562/8, 562/11, 12, 13, 20, 21; 540/484, 542

(56) References Cited

U.S. PATENT DOCUMENTS

| | | |
|---|---|---|
| 4,407,761 A | 10/1983 | Blum |
| 5,019,651 A | 5/1991 | Kieczykowski |
| 5,659,035 A * | 8/1997 | Bamber et al. ............... 546/22 |
| 5,908,959 A | 6/1999 | Kubela et al. |
| 2001/0041690 A1 | 11/2001 | Cazer et al. |

FOREIGN PATENT DOCUMENTS

DE 3700772 * 7/1988
WO WO 01/57052 A 8/2001

OTHER PUBLICATIONS

CA:114:102393 abs of AU599950 Aug. 1990.*
WPI Abstract Accession No. 1998–044166/05 of EP 08139021 A1, Dec. 29, 1997, "Process for the treatment of fertilisers by hydrophobe compostions in view of their bulk storage.", Navascues, et al., 1998.
WPI Abstract Accession No. 1982–35329E/18 of DD 0152352 AA, Nov. 25, 1981, "Radiation–hardenable unsatd. polyester resin compsn.—contg. stabiliser and sensitiser mixt. added before stabilised photoinitiator mixt.", Vechenstedt, et al., 1982.
WPI Abstract Accession No. 1977–70039Y/39 of JP 520034746 B May 9, 1977, "Electrolytic soln. for driving electrolysis condenser—comprises ethylene glycol based solvent contg. ammonium formate phosphorous acid, triethylamine and ammonium maleate.", 1997.
WPI Abstract Accession No. 1973–67377U/44 & JP 480035948B, Oct. 31, 1973, "Polyester prodn—by polycondensation, in presence of nitrogen–contg cpd and strong protonic acid", 1973.

* cited by examiner

Primary Examiner—Jean F. Vollano
(74) Attorney, Agent, or Firm—Frishauf, Holtz, Goodman & Chick, P.C.

(57) ABSTRACT

In a method for making bisphosphonates by reacting a carbonyl compound with a phosphorus halide, the reaction is carried out in a solvent/carrier system which is a mixture of an amine hydrochloride, phosphorous acid and optionally phosphoric acid.

10 Claims, No Drawings

SOLVENT SYSTEMS

BACKGROUND

This invention relates to improved solvent systems, and in particular to a solvent system for use in the production of bisphosphonate compounds.

Bisphosphonate compounds have generally been made by the reaction of carbonyl compounds with phosphorus halides. It is known in the art to use a variety of different carriers/solvents in the production of bisphosphonate compounds. However, all of the carriers/solvents used to date demonstrate major disadvantages, as to their use.

It is known from U.S. Pat. No. 4,407,761 to use chlorobenzene to attempt to solubilize the reaction. However, this method generates a high amount of an amorphous orange solid termed "orange pyrophoric solid" containing phosphorus and oxidised phosphorus. Orange pyrophoric solid is difficult to handle and as such is an undesirable by-product.

It is known from WO 98/34940 to use long chain glycols as carriers/solvents, to attempt to stop, the aforementioned solidification. However, solidification of the reaction still occurs and the long chain glycols cannot be recycled as they have been converted to chloride derivatives.

It is also known from U.S. Pat. No. 5,019,651 to use methane sulphonic acid as a carrier/solvent to overcome the aforementioned solubility difficulties. However, orange pyrophoric solid is again formed and the methane sulphonic acid cannot be recycled as it has been converted into methane sulphonyl chloride.

It is, therefore, desirable in the production of bisphosphonates to provide a carrier/solvent which does not lead to the formation of orange pyrophoric solid, which can be recycled and which does not cause solidification of the reaction.

BRIEF DESCRIPTION

Accordingly, the present invention provides a carrier/solvent system for the reaction of a carbonyl compound with a phosphorus halide to produce bisphosphonates, said system comprising an amine hydrochloride, phosphorous acid and optionally phosphoric acid.

The present invention also provides a bisphosphonate produced by means of the reaction of a carbonyl compound with a phosphorus halide, in the carrier/solvent system described in the immediately-preceding paragraph.

The carrier/solvent system may be formed in situ during the reaction.

The in situ production of this carrier/solvent system is believed to be novel. It is also surprising, as amine hydrochloride, phosphorous acid and neat phosphoric acid, as well as many carbonyl compounds, tend to be solids at ambient temperatures.

DETAILED DESCRIPTION

The amine hydrochloride may be a hydrochloride of a $C_1$–$C_8$ primary, secondary or tertiary amine, including isomers of those amines.

The amine hydrochloride is preferably tripropylamine hydrochloride. Alternatively, the amine hydrochloride may be triethylamine hydrochloride, tributylamine hydrochloride or trimethylamine hydrochloride.

Phosphorous acid ($H_3PO_3$) may conveniently be generated in situ by the reaction of $PCl_3$ and water. Phosphoric acid ($H_3PO_4$) may conveniently be generated in situ by the reaction of $POCl_3$ and water.

The carbonyl compound used in the reaction according to the present invention can be represented by the general chemical formula:

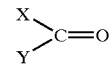

wherein X is a hydroxyl, amine, ester or halide;
Y is R or $R^1$ wherein R is a $C_1$–$C_8$ alkyl group and $R^1$ is a $C_1$–$C_8$ amine, ether, pyridyl or sub amino group.
X and Y may also together form a cyclic ring, in which one of X or Y is aza.

The carbonyl compound may therefore be a substituted acid e.g. an amino acid.

The phosphorus halide is preferably a phosphorus trihalide. The phosphorus trihalide is preferably phosphorus trichloride. Alternatively, the phosphorus trihalide may be phosphorus tribromide.

The bisphosphonate end product may be generally represented by the chemical formula:

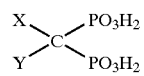

wherein X is a hydroxyl group and Y is R or $R^1$ wherein R is a $C_1$–$C_8$ alkyl group and $R^1$ is a $C_1$–$C_8$ amine, ester, pyridyl or sub-amino group.

X and Y may also together form a cyclic ring structure in which one of X or Y is aza.

The relative amounts of the components in the reaction mixture will depend on the physical and chemical properties of the carbonyl compound which is being phosphonated and other usual considerations. The best results for any particular carbonyl system can be determined with a small amount of routine experimentation. However, in general we have found that the following ratios are effective:

Ratio of AMINE HYDROCHLORIDE to PHOSPHOROUS ACID: from 3:1 to 8:1
Ratio of AMINE HYDROCHLORIDE to PHOSPHORIC ACID: from 0.8:1 to 2.5:1
Ratio of CARBONYL COMPOUND to PHOSPHOROUS ACID: from 0.5:1 to 1.5:1

The above ratios are molar and represent the theoretical amount to be used in the system, either by direct addition or by generation in situ of the respective acid.

An embodiment of the invention will now be described with reference to the following examples.

EXAMPLE 1

Neridronic Acid—1 Liter Preparation

A 1-liter jacketed vessel fitted with an overhead stirrer and a condenser with an outlet to a scrubbing system for hydrogen chloride (HCl) gas was charged with 110 g of concentrated hydrochloric acid. 243 g of tripropylamine was then added slowly via a dropping funnel whilst the reaction temperature was maintained below 50° C. 0.45 moles of 6-amino caproic acid was then added to the vessel, followed by subsequent slow addition of 155 g of $POCl_3$ at a temperature of 60–65° C. The reaction was exothermic. 150 g of $PCl_3$ was then slowly added to the vessel, maintaining the temperature at 60° C. The mixture in the vessel was then heated slowly to 100° C. and maintained at this temperature for 3 hours. The mixture was then hydrolysed by dropping into 250 g of water and refluxing for 6 hours. The end product was isolated by standard methods known in the art to give 80 g of a white crystalline solid (64% yield, based on the weight of amino acid used).

EXAMPLE 2

Alendronic Acid—1 Liter Preparation

A 1 liter jacketed vessel fitted with an overhead stirrer and a condenser with an outlet to a scrubbing system for hydrogen chloride (HCl) gas was charged with 110 g of concentrated hydrochloric acid. 243 g of tripropylamine was then added slowly via a dropping funnel whilst the reaction temperature was maintained below 50° C. 0.45 moles of 4-aminobutyric acid was then added to the vessel, followed by subsequent slow addition of 130 g of $POCl_3$ at a temperature of 60–65° C. The reaction was exothermic. 245 g of $PCl_3$ was then slowly added to the vessel, maintaining the temperature at 60° C. The mixture in the vessel was then heated slowly to 90° C. and maintained at this temperature for 3 hours. The mixture was then hydrolysed by dropping into 250 g of water and refluxing for 6 hours. The end product was isolated by standard methods known in the art to give 89.7 g of a white crystalline solid (61% yield, based on the weight of amino acid used).

EXAMPLE 3

Azacycloheptane-1,1-diphosphonic Acid—50 Gallon Preparation

A 50 gallon oil jacketed glassed steel vessel, fitted with an overhead stirrer, a condenser with an outlet to a scrubbing system for hydrogen chloride (HCl) gas and a nitrogen purge, was charged with 42.1 kg of concentrated hydrochloride acid. 93 kg of tripropylamine was then added slowly via a dropping funnel whilst the reaction temperature was maintained below 50° C. 19.5 kg of caprolactam was then added to the vessel, followed by subsequent slow addition of 59.8 kg of $POCl_3$ at a temperature of 60 to 65° C. The reaction was exothermic. 71.2 kg of $PCl_3$ was then slowly added to the vessel, maintaining the temperature at 60° C. The mixture in the vessel was then heated slowly to 90° C. and maintained at this temperature for 3 hours. The mixture was then hydrolysed by dropping into 115 kg of water and refluxing for 1 hour. The end product was isolated by standard methods known in the art to give 27.4 kg of a white crystalline solid (61% yield, based on the weight of amino acid used).

What is claimed is:

1. A method for the production of a bisphosphonate of formula (I)

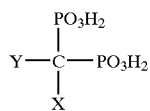

(I)

wherein: X=OH
   Y=R or $R_1$
   R=$C_1$ to $C_8$ alkyl
   $R_1$=$C_1$ to $C_8$ amine, ester or pyridyl
or X and Y together form a cyclic structure wherein one of X and Y is represents an aza group;

by reacting a carbonyl compound of general formula:

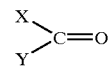

wherein: X=OH, amine, ester or halide
   Y=R or $R_1$
   R is $C_1$ to $C_8$ alkyl
   $R_1$ is $C_1$ to $C_8$ amine, ether or pyridyl
or X and Y together form a cyclic structure wherein one of X and Y represents an aza group,
with a phophorus halide, in a carrier/solvent system consisting essentially of
   (a) an amine hydrochloride
   (b) phosphorous acid
   (c) phosphoric acid,
and wherein said method does not produce any orange pyrophoric solid.

2. The method of claim 1, further comprising forming said phosphorous acid and/or said phosphoric acid in situ during said reaction.

3. The method of claim 1, wherein said amine hydrochloride (a) is a hydrochloride of an amine selected from the group consisting of
   (i) $C_1$–$C_8$ primary amines
   (ii) $C_1$–$C_8$ secondary amines
   (iii) $C_1$–$C_8$ tertiary amines and
   (iv) isomers of said amines (i) (ii) or (iii).

4. The method of claim 3, wherein said amine hydrochloride (a) is selected from the group consisting of
   (i) tripropylamine hydrochloride
   (ii) triethylamine hydrochloride
   (iii) tributylamine hydrochloride and
   (iv) trimethylamine hydrochloride.

5. The method of claim 1, wherein said phosphorus halide is a phosphorus trihalide.

6. The method of claim 5, wherein said phosphorus trihalide is selected from the group consisting of phosphorus trichloride and phosphorus tribromide.

7. The method of claim 1, wherein a molar ratio of the components of the carrier/solvent system is as follows:
   Ratio of AMINE HYDROCHLORIDE to PHOSPHOROUS ACID: from 3:1 to 8:1
   Ratio of AMINE HYDROCHLORIDE to PHOSPHORIC ACID: from 0.8:1 to 2.5:1
   Ratio of CARBONYL COMPOUND to PHOSPHOROUS ACID: from 0.5:1 to 1.5:1.

8. The method of claim 7, wherein
   (a) said amine hydrochloride is a hydrochloride of an amine selected from the group consisting of
      (i) tripropylamine hydrochloride
      (ii) triethylamine hydrochloride
      (iii) tributylamine hydrochloride and
      (iv) trimethylamine hydrochloride;
   (b) said carbonyl compound has the formula

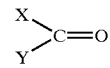

where:
   X is selected from the group consisting of hydroxyl, amine, ester and halide;
   Y is selected from the group consisting of
   R and $R^1$, in which
   R denotes a $C_1$–$C_8$, alkyl entity and $R^1$ denotes an entity selected from the group consisting of
(i) $C_1$–$C_8$ amines
(ii) $C_1$–$C_8$ ethers and
(iii) $C_1$–$C_8$ pyridyl entities.

9. The method of claim 6, further comprising forming said phosphorous acid and/or said phosphoric acid in situ during said reaction.

10. The method of claim 1, wherein said carbonyl compound is selected from the group consisting of caprolactam, 4-amino butyric acid, 6-aminocaproic acid, 3-pyridylacetic acid, beta-amino propionic acid, 3-N,N-dipentylaminopropionic acid.

* * * * *